United States Patent [19]

Rodrigues Claro

[11] Patent Number: 5,893,843
[45] Date of Patent: Apr. 13, 1999

[54] POTENTIOMETER-CONTROLLED FLUID EJECTION DEVICE

[76] Inventor: Jorge Antônio Rodrigues Claro, Rua Whately, 536, Resende, 27542-170, RJ, Brazil

[21] Appl. No.: 08/801,080

[22] Filed: Feb. 14, 1997

[51] Int. Cl.⁶ ............................................. A61M 37/00
[52] U.S. Cl. ........................... 604/132; 604/153; 604/154
[58] Field of Search ............................. 417/415, 437; 604/131, 132, 153, 154; 128/DIG. 12

[56] References Cited

U.S. PATENT DOCUMENTS

| | | | |
|---|---|---|---|
| 2,761,445 | 9/1956 | Cherkin | 604/132 |
| 4,033,479 | 7/1977 | Fletcher et al. | 222/61 |
| 4,155,362 | 5/1979 | Jess | 128/214 F |
| 4,337,769 | 7/1982 | Olson | 128/214 F |
| 4,346,705 | 8/1982 | Pekkarinen et al. | 128/214 F |
| 4,479,760 | 10/1984 | Bistad et al. | 417/395 |
| 4,626,243 | 12/1986 | Singh et al. | 604/141 |
| 4,650,469 | 3/1987 | Berg et al. | 604/131 |
| 4,718,576 | 1/1988 | Tamura et al. | 222/63 |
| 4,919,649 | 4/1990 | Timothy et al. | 604/65 |
| 5,000,739 | 3/1991 | Kulisz et al. | 604/132 |
| 5,078,682 | 1/1992 | Miki et al. | 604/65 |
| 5,127,908 | 7/1992 | Walker et al. | 604/153 |
| 5,167,633 | 12/1992 | Mann et al. | 604/141 |
| 5,207,645 | 5/1993 | Ross et al. | 604/141 |
| 5,232,439 | 8/1993 | Campbell et al. | 604/28 |
| 5,248,300 | 9/1993 | Bryant et al. | 604/134 |
| 5,281,202 | 1/1994 | Weber et al. | 604/132 |
| 5,308,333 | 5/1994 | Skakoon | 604/126 |
| 5,318,540 | 6/1994 | Athayde et al. | 604/141 |
| 5,330,431 | 7/1994 | Herskowitz | 604/153 |
| 5,342,313 | 8/1994 | Campbell et al. | 604/153 |
| 5,348,539 | 9/1994 | Herskowitz | 604/141 |
| 5,411,482 | 5/1995 | Campbell | 604/153 |
| 5,423,747 | 6/1995 | Amano | 604/65 |
| 5,423,759 | 6/1995 | Campbell | 604/153 |
| 5,578,001 | 11/1996 | Shah | 604/31 |

*Primary Examiner*—Wynn Wood Coggins
*Assistant Examiner*—Deborah Blyveis
*Attorney, Agent, or Firm*—Webb Ziesenheim Bruening Logsdon Orkin & Hanson, P.C.

[57] ABSTRACT

A potentiometer-controlled electromechanic system to eject fluids by squeezing flexible plastic containers. The system comprises an electromechanic driving set, including an electric motor-driven shaft with a worm gear engaged to rack gear sections of arms attached to a movable presser plate, that squeeze a fluid-containing flexible plastic bag inserted in a cavity formed at the front portion of the device housing. The cavity is formed by a movable presser plate and a fixed clear and transparent front plate, bent at its sides. The fluid ejection parameters are controlled by an electronic set comprising a precision potentiometer attached to the motor-driven shaft, linked to a microprocessor-based electronic circuitry and a programming set formed by a series of buttons for entering the required ejection parameters, such as fluid flow rate, pressure, ejected volume, etc. The parameters are visualized in a liquid-crystal display. During the ejection procedure, the motor-driven shaft speed is monitored by the precision potentiometer, whose electric impulses are compared, at the central processing unit, to the entered required parameters. The central processing unit calculates the needed electric motor torque and rotation speed and the operating time. The device is applicable to medical uses, to inject fluids contained in flexible plastic bags into a patient, at precisely controlled parameters, as well as other non-medical applications.

8 Claims, 4 Drawing Sheets

POTENTIOMETER-CONTROLLED FLUID EJECTION DEVICE

BACKGROUND OF THE INVENTION

The invention relates to a method of fluid ejection under controlled parameters, such as flow rate, pressure and volume, in a device intended to infuse fluids to patients, like those for intravenous, parenteral, enteral, antibiotics and other medical uses, as well as simply pumping fluids contained in flexible plastic bags.

Infusion fluids for medical use are generally supplied from flexible plastic containers attached to infusion tubings. The most common method is by passive, gravity-feed infusion, accomplished by suspending the bag from a pole, at a certain height relative to the patient. Sufficient pressure is created by gravity acting upon the fluid in the reservoir, with the flow rate being controlled by a manually operated valve. For these suspended bags, a flexible encasement with a chamber may be provided. Air is filled in the chamber at a given pressure, to increase the flow rate from the bag, with the pressure in the encasement being controlled by a manometer.

As an alternative to those gravity-feeding, low and unprecisely controlled flow rate devices, mechanically driven devices have been developed. The potential advantage of these mechanically induced pressure devices is the possibility to more precisely control the fluid ejection parameters, achieving at the same time, higher flow rates of fluids contained in flexible plastic containers for a wide range of applications. For example, Fletcher et al. U.S. Pat. No. 4,033,479 discloses an infusion device by mechanically pressing a fluid-containing reservoir at a constant pressure. Cherkin U.S. Pat. No. 2,761,445 describes a device containing a bag pressing platform moved by a variable speed motor. Another example of flow controlled infusion devices for squeezing a flexible bag is described by Campbell, U.S. Pat. No. 5,232,439 and U.S. Pat. No. 5,423,759, which describes an infusion pump and a valve system for its control. The infusion tubing is mechanically closed depending on the pressure of the fluid in the bag measured by a sensor pressed against the outside of the reservoir by a presser plate.

It is an object of the present invention to provide a simple and precise method to eject and control the fluid discharge parameters, eg., volume, flow rate and the pressure needed to achieve it. The invention includes a precision potentiometer attached to a motor driven shaft with a worm gear. The precision potentiometer continuously detects shaft rotation speed. This value is compared to the calculated parameters in a central processing unit (CPU), taking into account the operator entered required parameters by means of input buttons. The required parameters may be visualized in a liquid-crystal display. This computer assisted, precision potentiometer controlled, fluid-contained flexible bag squeezing device, is potentially simpler and more precise than previous devices, due to its capability to better control the squeezing pressure on the bag. The precision potentiometer controls the motor-driven shaft rotation speed. The CPU can precisely control the electric current to the motor, thereby controlling motor speed and torque, with assistance of a microprocessor-based circuit and appropriate software. The desired flow rate may thereby be achieved.

Other and additional objects are apparent from the following discussion of the invention and its preferred embodiment.

SUMMARY OF THE INVENTION

The present invention simplifies the infusion procedure for medical fluids by providing a precision potentiometer-controlled device for squeezing ready to use flexible plastic bags. The bag to be infused is inserted between a fixed, clear and transparent front plate bent at its sides in the front end of the device housing and a motor driven presser plate. The fixed, clear and transparent front plate bent at its sides permits the operator to monitor the fluid in the bag for air bubbles and the initial procedure to evacuate the air in the container. Using input buttons and a liquid crystal display in the device, the operator is able to enter the required fluid discharge parameters, such as flow rate and ejected volume. A central processing unit then calculates the needed motor driven shaft speed and torque to achieve the desired parameters. On start-up and during operation, the precision potentiometer continuously monitors the motor-driven shaft speed and sends appropriate electric signals to the processing unit, which compares them to the calculated values. The processing unit controls the electric current to the motor to maintain the precise and necessary motor-driven shaft speed and torque, until the desired volume of medical fluid is ejected at the required flow rate and calculated ejection timing.

The present invention provides a fluid-containing flexible bag squeezing device, simple to use and with sufficient precision for medical use, as well as for other applications where a predetermined fluid ejection flow rate is desirable.

The present invention also provides a more complete arrangement for high precision medical injecting procedures not only for intravenous, parenteral and enteral fluids, but also for contrast media contained in flexible plastic bags, employing multi-phase protocols. In these cases, a large capacity central processing unit and software, and a liquid crystal display, can be included to be operator programmed, showing all desired injection parameters, like fluid flow rate and volume for each phase, needed pressure, interphase delays, injection time interval, etc.

DETAILED DESCRIPTION OF THE PREFERRED EMBODIMENT

Figure 1:
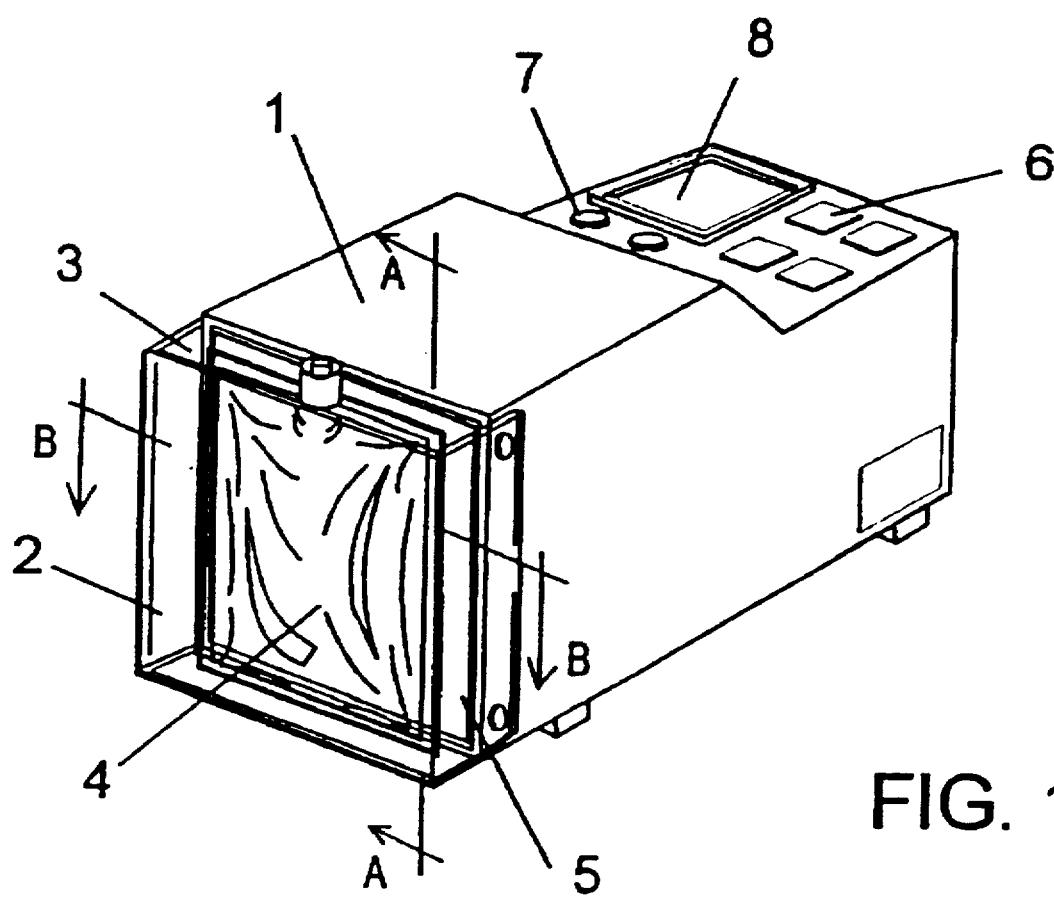
FIG. 1 is an outer view of the basic preferred embodiment of the present invention.

The preferred embodiment of the present invention in its basic configuration is depicted in FIGS. 1–4. FIG. 5 shows the flow chart of the basic sequences of operation of the system.

The preferred embodiment is a fluid ejection device 1 to eject fluids from flexible plastic bags for several medical uses, such as intravenous and intra-crystal therapeutic fluids, direct injection in the human body cavities, injecting diagnostic fluids (eg., contrast media), as well as ejecting fluids for other non-medical applications, when a given fluid flow rate and predetermined volume are desired.

The front portion of the device contains a fixed clear and transparent plate 2 bent at its sides, forming a cavity 3, where a flexible, fluid-containing bag 4 is positioned. Completing this cavity 3 is an electric motor-driven presser plate 5 to squeeze the bag against the fixed clear and transparent plate 2 bent at its sides. The rear portion of the device contains a series of controls, such as indicator lights and input buttons for programming squeezing parameters, generally represented in FIG. 1 by input 6 and indicator lights 7. Input button 6 and indicator lights 7 are exemplary and not intended in any way to limit the number and type of controls. Liquid crystal display 8 is able to show the programmed ejection parameters before start, the parameters during the fluid ejection in progress, as well as the achieved parameters at the completion of the procedure.

Figure 2:
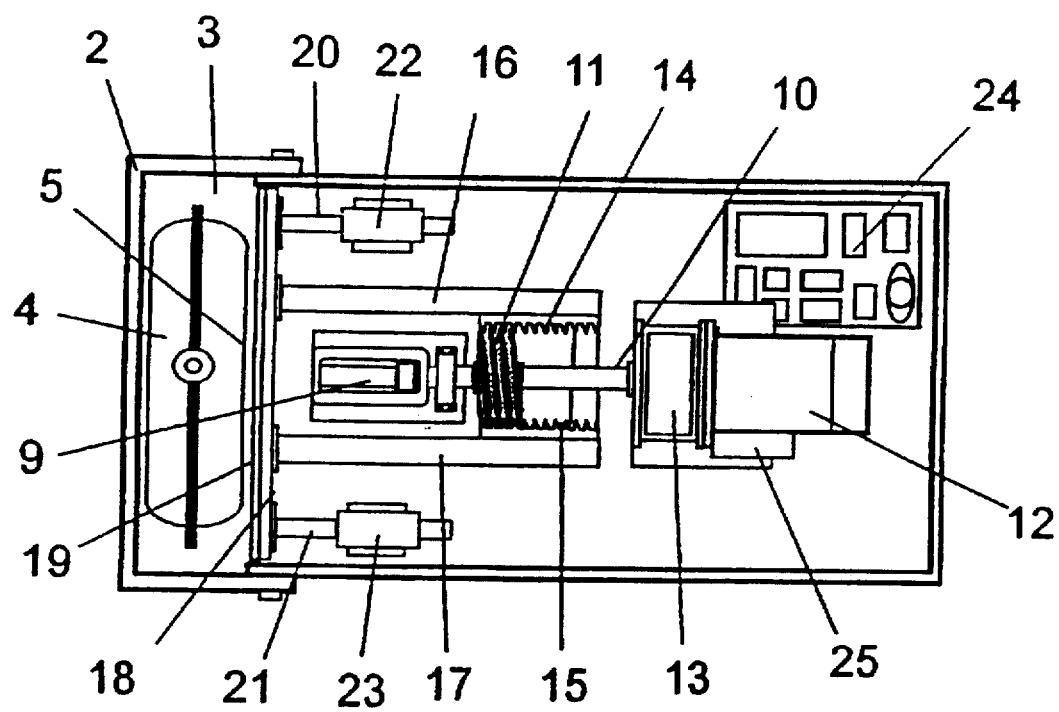
FIG. 2 is a cross-sectional view of the preferred embodiment, taken at section line A—A in FIG. 1, shown with the fluid-containing flexible bag.

As shown in FIG. 2, a precision potentiometer 9 is attached to a motor-driven shaft 10, and controls said motor-driven shaft rotation speed. Electric motor 12 and reduction gear 13 are coupled with motor-driven shaft 10. The worm gear 11 is engaged to rack gear sections 14 and 15 at the rear ends of arms 16 and 17, the front ends of said arms being attached to the movable presser plate 5. Presser plate 5 is formed by a rigid plate 18 and a rubber-type coating material 19, with high friction properties to facilitate the flexible bag fixing and positioning in the cavity 3. The bag 4 is squeezed against the fixed clear and transparent front plate 2 bent at its sides. To maintain the preferred parallel alignment between the plates 2 and 5, the presser plate 5 is maintained vertically aligned and supported by lateral bars 20 and 21, sliding in supporting rings 22 and 23. The electric impulses from the precision potentiometer 9 are sent to a processing circuit board 24, where they are compared to the operator entered desired parameters. Processing circuit board 24 controls the electric current intensity to the driving motor 12 by a current control element 25, to produce the required rotation speed and torque of the motor-driven shaft 10.

Figure 3:
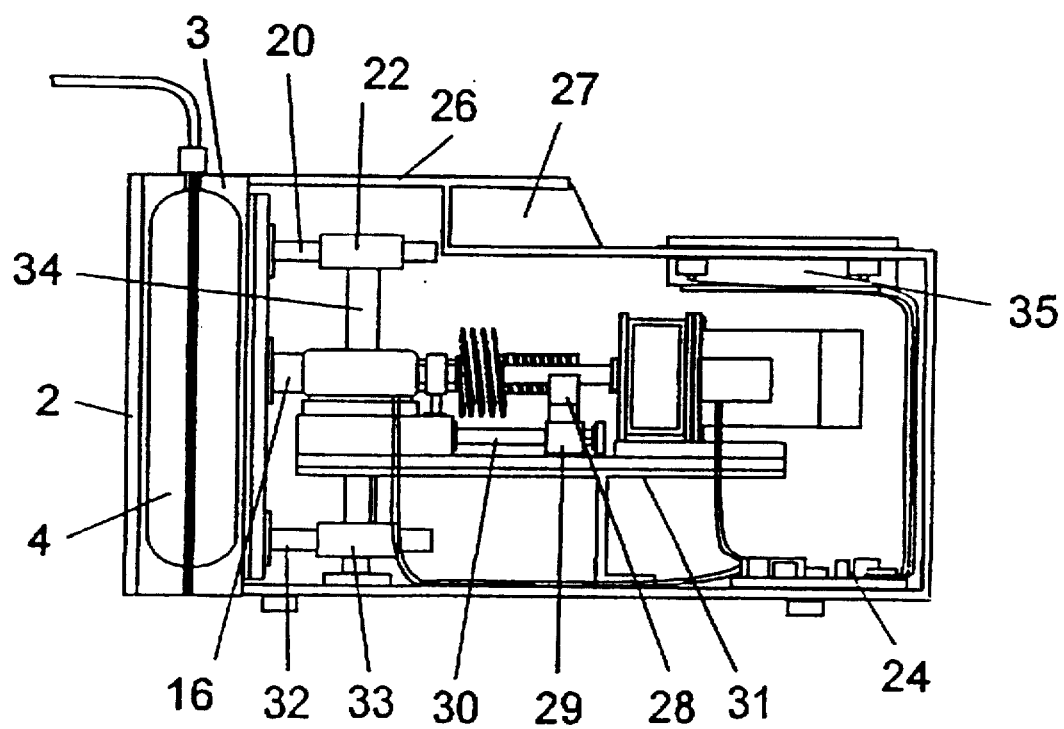
FIG. 3 is a cross-sectional view of the preferred embodiment, taken at section line B—B in FIG. 1.

Now referring specifically to FIG. 3, the preferred embodiment contains an outer encasement 26 with a cavity 27 to facilitate hanging up the device when needed for transport and positioning. The rear ends of arms 16 and 17 are linked and additionally supported by supporting member 28, whose lower ring 29 is able to slide along a bar 30 fixed to a basic structure 31 to additionally maintain the precise positioning and alignment of the pressing set. The preferred parallel alignment of the movable presser plate 5 relative to the fixed clear and transparent front plate 2 bent at its sides is kept through positioning sets comprising bars 20 and 32 sliding inside guide rings 22 and 33 fixed to a support member 34, with the other set not visible in the figure.

The microprocessor-based circuit board 24 is electrically linked to the precision potentiometer 9 and a programming board set 35, that contains the indicator lights 7 and input buttons 6, and the liquid crystal display 8, forming the device control set.

Figure 4:
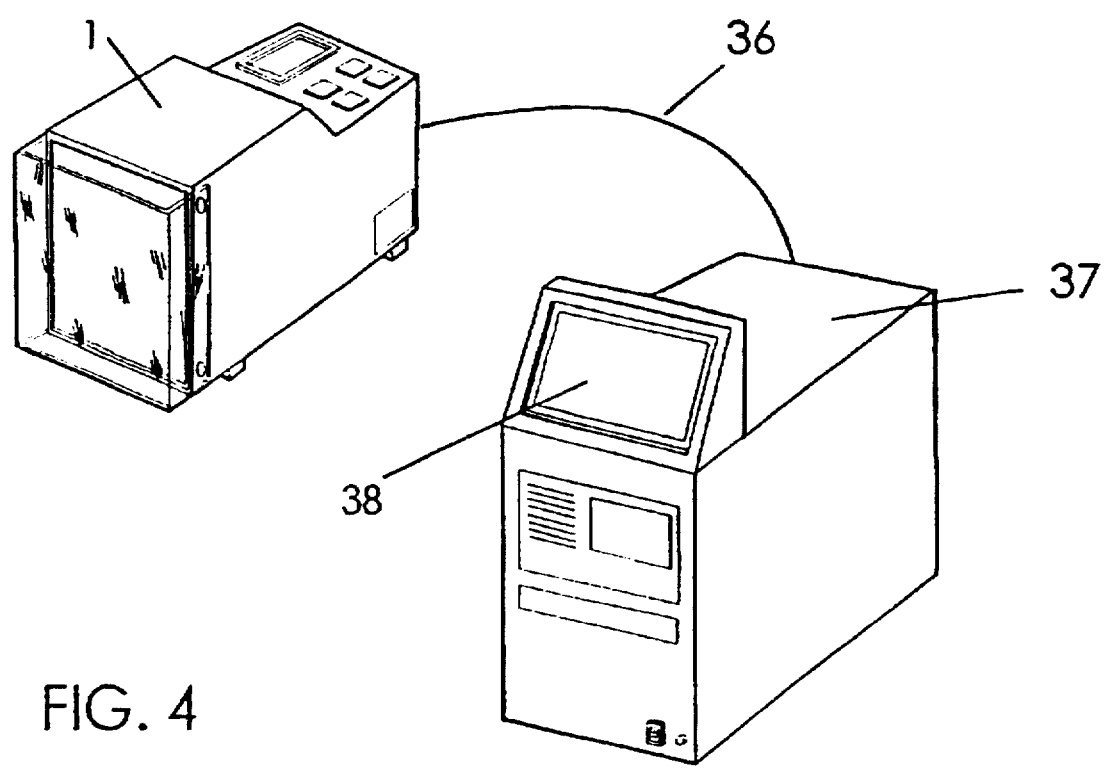
FIG. 4 is an outer view of the high precision multiphasic contrast media injection set, shown with the squeezing bag power head and the central processing unit and liquid crystal display.
Figure 5:
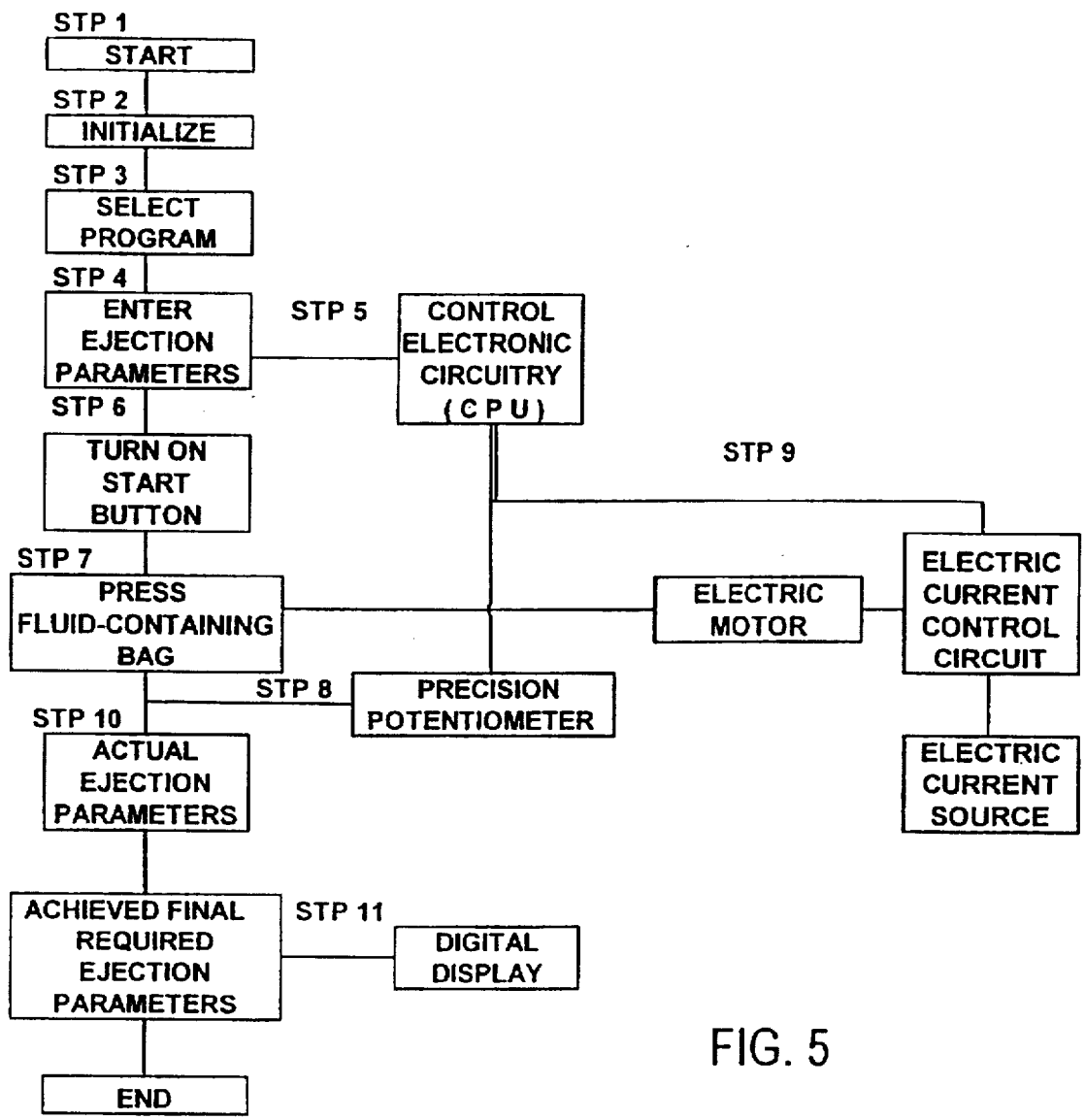
FIG. 5 is a flow chart of the operation sequences of the preferred embodiment of the present invention.

FIG. 4 shows the fluid-containing flexible bag squeezing device 1 electrically linked by wiring 36 to a large, external processing unit 37 and liquid crystal display 38, in an arrangement to attend the requirements for complex fluid ejection protocols, including multi-phasic ejection resources. The operation of the device, however, remains the same as in the preferred embodiment described in respect of FIGS. 1, 2 and 3.

FIG. 5 shows a flow chart of the general steps involved in the operation of the present invention, with start, initialize and select program steps 1, 2 and 3, the ejection parameters being entered in a step 4, and visualized in the liquid crystal display. The required ejection parameters are then electronically transferred in a step 5 to the control electronic circuitry (central processing unit). In a step 6 the ejection procedure is started by turning on a command button to initialize the pressing action and squeezing the flexible fluid-containing bag. The pressing action in a step 7 represents the displacement of the movable pressing plate 5, whose speed and force are determined by the rotation speed and torque of the motor-driven shaft 10. The precision potentiometer controls the ejection parameters in a step 8 measuring the motor-driven shaft speed, sending impulses to the CPU. The CPU compares the impulses to the calculated values from the entered required parameters, and sends, as a result, command impulses, in a step 9, to the electric current control circuit that controls the electric current intensity to the motor. The actual ejection parameters are continuously presented in a step 10 in the liquid crystal display. Once the final required fluid ejected volume is achieved, the driving set is stopped, with the achieved final required ejection parameters remaining in a step 11 presented on a liquid crystal display.

Although the present invention has been described and detailed according to the preferred embodiment it is understood that many modifications and variances may be made therein without departing from the scope of the appended claims.

What is claimed is:

1. An infusion device for delivering fluid from a flexible plastic container, the infusion device comprising:

a receptacle for the flexible plastic container;

a fixed, clear and transparent front plate, bent at its sides to contact one side of the container;

a movable plate to contact and press the other side of the container, the movable plate having a high friction rubber-type coating to keep the container in place, the movable plate positioned in an essentially parallel alignment with the fixed, clear and transparent front plate bent at its sides, to squeeze the container from its middle surface area;

an electromechanical driving set to advance and retract the movable plate; and an electronic control set comprising a precision potentiometer linked to an electronic circuitry and software and to a liquid crystal display, to control a motor-driven shaft rotation speed.

2. The invention of claim 1, wherein the receptacle for receiving the container is defined by the fixed, clear and transparent front plate bent at its sides, and by the movable plate; said fixed front plate bent at its sides being clear and transparent to permit the visual inspection of the fluid in the container for the presence of air bubbles and their withdrawal.

3. The invention of claim 1, wherein the driving set comprises an electrical motor and a reduction gear box driving said shaft, said shaft attached to a worm gear at its mid portion, said worm gear driving at least one rack gear section.

4. The invention of claim 3, further comprising parallel arms having a front end attached to the movable pressing plate, and rear ends containing rack gear sections fitted to the worm driving gear.

5. The invention of claim 3, wherein said motor-driven shaft has a front end attached to the potentiometer.

6. The invention of claim 1, wherein the liquid crystal display shows fluid ejection parameters, including but not limited to flow rate, pressure, ejected volume, and container size, said liquid crystal display having a tilting capability.

7. The invention of claim 1, wherein the electronic circuitry and software controls an electric current to an electric motor based on fluid ejection parameters compared to impulses generated by the precision potentiometer and values calculated based on pre-programmed parameters.

8. A potentiometer controlled infusion device to eject fluid by squeezing flexible, fluid-containing plastic bags, comprising:

a housing having a fixed, clear and transparent front plate, bent at its sides to form a receptacle to accommodate the fluid-containing bag, said receptacle further defined by a movable plate having an essentially parallel alignment and displacement relative to the fixed plate;

said housing further defining an upper cavity to facilitate transport of the device by hanging it up;

a liquid crystal display to show entered and achieved fluid ejection parameters, said liquid crystal display having a tilting capability; and an electronic control set comprising a precision potentiometer and electronic circuitry and software to control an electric motor rotation speed and torque by adjusting an electric current intensity feeding the motor.

* * * * *

UNITED STATES PATENT AND TRADEMARK OFFICE
CERTIFICATE OF CORRECTION

PATENT NO. : 5,893,843
DATED : April 13, 1999
INVENTOR(S) : Jorge Antônio Rodrigues Claro It is certified that error appears in the above-identified patent and that said Letters Patent is hereby corrected as shown below:

Title Page, after filing date insert
   --[30] Foreign Application Priority Data
      Feb. 14, 1996 [BR]  Brazil..........9600722--.

Column 2 Line 61 "intra-crystal" should read --intra-arterial--.

Column 2 Line 63 "eg." should read --e.g.--.

Column 3 Line 3 after "fixed" insert comma --,--.

Column 3 Line 7 "input 6" should read --input buttons 6--.

Column 3, Line 8 "Input button" should read --Input buttons--.

Signed and Sealed this

Fourteenth Day of September, 1999

Attest:

Q. TODD DICKINSON

*Attesting Officer*    *Acting Commissioner of Patents and Trademarks*